(12) United States Patent
Glenn et al.

(10) Patent No.: US 10,444,980 B1
(45) Date of Patent: Oct. 15, 2019

(54) BIOMECHANICAL MOTION MEASUREMENT AND ANALYSIS FOR SELF-ADMINISTERED TESTS

(71) Applicant: The Cognitive Healthcare Company, San Francisco, CA (US)

(72) Inventors: Shenly Glenn, San Francisco, CA (US); Joel Mefford, Benicia, CA (US)

(73) Assignee: THE COGNITIVE HEALTHCARE COMPANY, San Francisco, CA (US)

( * ) Notice: Subject to any disclaimer, the term of this patent is extended or adjusted under 35 U.S.C. 154(b) by 0 days.

(21) Appl. No.: 14/882,393

(22) Filed: Oct. 13, 2015

Related U.S. Application Data

(60) Provisional application No. 62/062,988, filed on Oct. 13, 2014.

(51) Int. Cl.
| | | |
|---|---|---|
| *G06F 3/041* | (2006.01) | |
| *A61B 5/00* | (2006.01) | |
| *G06F 3/0488* | (2013.01) | |
| *G06K 9/00* | (2006.01) | |
| *G16H 50/30* | (2018.01) | |

(52) U.S. Cl.
CPC ........ *G06F 3/04883* (2013.01); *A61B 5/4064* (2013.01); *A61B 5/4082* (2013.01); *A61B 5/4088* (2013.01); *A61B 5/6898* (2013.01); *G06F 3/0412* (2013.01); *G06F 3/04886* (2013.01); *G06K 9/00355* (2013.01); *G16H 50/30* (2018.01); *G06F 2203/04803* (2013.01); *G06F 2203/04808* (2013.01)

(58) Field of Classification Search
CPC ............... G06F 3/04883; G06F 3/0412; G06F 3/04886; G06F 19/3431; G06F 2203/04808; G06F 2203/04803; A61B 5/4064; A61B 5/4088; A61B 5/4082; A61B 5/6898; G06K 9/00355
USPC .......................................................... 345/173
See application file for complete search history.

(56) References Cited

U.S. PATENT DOCUMENTS

| | | | |
|---|---|---|---|
| 5,956,671 | A | 9/1999 | Ittycheriah et al. |
| 8,606,581 | B1 | 12/2013 | Quast et al. |
| 8,781,831 | B2 | 7/2014 | Ljolje et al. |
| 8,830,189 | B2 * | 9/2014 | Rimon .................... G06F 3/044 345/173 |

(Continued)

*Primary Examiner* — Vinh T Lam
(74) *Attorney, Agent, or Firm* — Redbrick IP, P.C.

(57) ABSTRACT

A client device is configured with a test administration application for conducting self-administered tests. A user interface of the test administration application includes motion restriction regions configured to prevent select types of body motion during particular segments of self-administered tests, and testing regions configured to receive a touch input performed by a specific digit of the user. For example, a touch input involves touching, holding, or tapping a single digit within the bounds of a testing region in accordance with instructions provided by the test administration application. The test administration module records motion data comprising one or more touch events, each touch event describing a touch input performed by the user. Undesired touch inputs that may obscure or degrade the reliability of biomechanical data are identified. The test administration module determines whether a user has successfully completed the test in accordance with instructions provided by the test administration application.

16 Claims, 11 Drawing Sheets

(56) References Cited

U.S. PATENT DOCUMENTS

| | | | | |
|---|---|---|---|---|
| 8,856,543 B2* | 10/2014 | Geiger | | G06F 21/32 |
| | | | | 713/186 |
| 8,866,752 B2* | 10/2014 | Westerman | | G06F 3/0235 |
| | | | | 345/173 |
| 9,063,647 B2* | 6/2015 | Zotov | | G06F 3/0416 |
| 9,075,462 B2* | 7/2015 | Sauer | | G06F 3/041 |
| 9,092,125 B2* | 7/2015 | Michaelis | | G06F 3/04845 |
| 9,141,284 B2* | 9/2015 | Sands | | G06F 3/042 |
| 9,147,059 B2* | 9/2015 | Isbister | | G06F 21/32 |
| 2005/0080592 A1 | 4/2005 | Buscema et al. | | |
| 2006/0132283 A1* | 6/2006 | Eberhart | | A61B 5/1171 |
| | | | | 340/5.2 |
| 2007/0298385 A1 | 12/2007 | Jenkins et al. | | |
| 2011/0066082 A1 | 3/2011 | Duffy | | |
| 2012/0030570 A1* | 2/2012 | Migos | | G06F 3/04883 |
| | | | | 715/702 |
| 2012/0330178 A1 | 12/2012 | Kraft et al. | | |
| 2013/0216986 A1 | 8/2013 | Goldman et al. | | |
| 2014/0026212 A1* | 1/2014 | Geiger | | G06F 3/04883 |
| | | | | 726/19 |
| 2014/0336539 A1* | 11/2014 | Torres | | A61B 5/11 |
| | | | | 600/595 |
| 2015/0213244 A1* | 7/2015 | Lymberopoulos | | G06F 21/32 |
| | | | | 726/18 |
| 2015/0242812 A1* | 8/2015 | Nelson | | G06Q 10/10 |
| | | | | 705/311 |
| 2016/0034738 A1* | 2/2016 | Luo | | G06K 9/001 |
| | | | | 382/125 |
| 2016/0063236 A1* | 3/2016 | Masuko | | G06F 21/31 |
| | | | | 726/18 |
| 2016/0357429 A1* | 12/2016 | Nilo | | G06F 3/0416 |

\* cited by examiner

400

| Time | Location | Event | Region | Action |
|---|---|---|---|---|
| $t_0$ | $x_1, y_1$ | FD | Restriction 1 | Record $1^{st}$ FD event; |
| $t_1$ | $x_2, y_2$ | FD | Restriction 2 | Record $2^{nd}$ FD event adjacent to $1^{st}$ FD event; |
| $t_2$ | $x_3, y_3$ | FD | Free 1 | Record $3^{nd}$ FD event adjacent to $2^{nd}$ FD event; |
| $t_3$ | $x_4, y_4$ | FD | Free 2 | Record $4^{th}$ FD event adjacent to $3^{rd}$ FD event; |
| $t_4$ | $x_5, y_5$ | FD | Target 1 | Record $5^{th}$ FD event in target region between Restriction 1 and Restriction 2 regions; |
| $t_5$ | $x_1, y_1$ | FM | Restriction 1 | Record FM event in Restriction 1 region |
| $t_6$ | $x_2, y_2$ | FM | Restriction 2 | Record FM event in Restriction 2 region |
| $t_7$ | $x_5, y_5$ | FU | Target 1 | Record FU event in Target 1 region |
| $t_8$ | $x_5, y_5$ | FD | Target 1 | Record FD event in Target 1 region |

FIG. 4

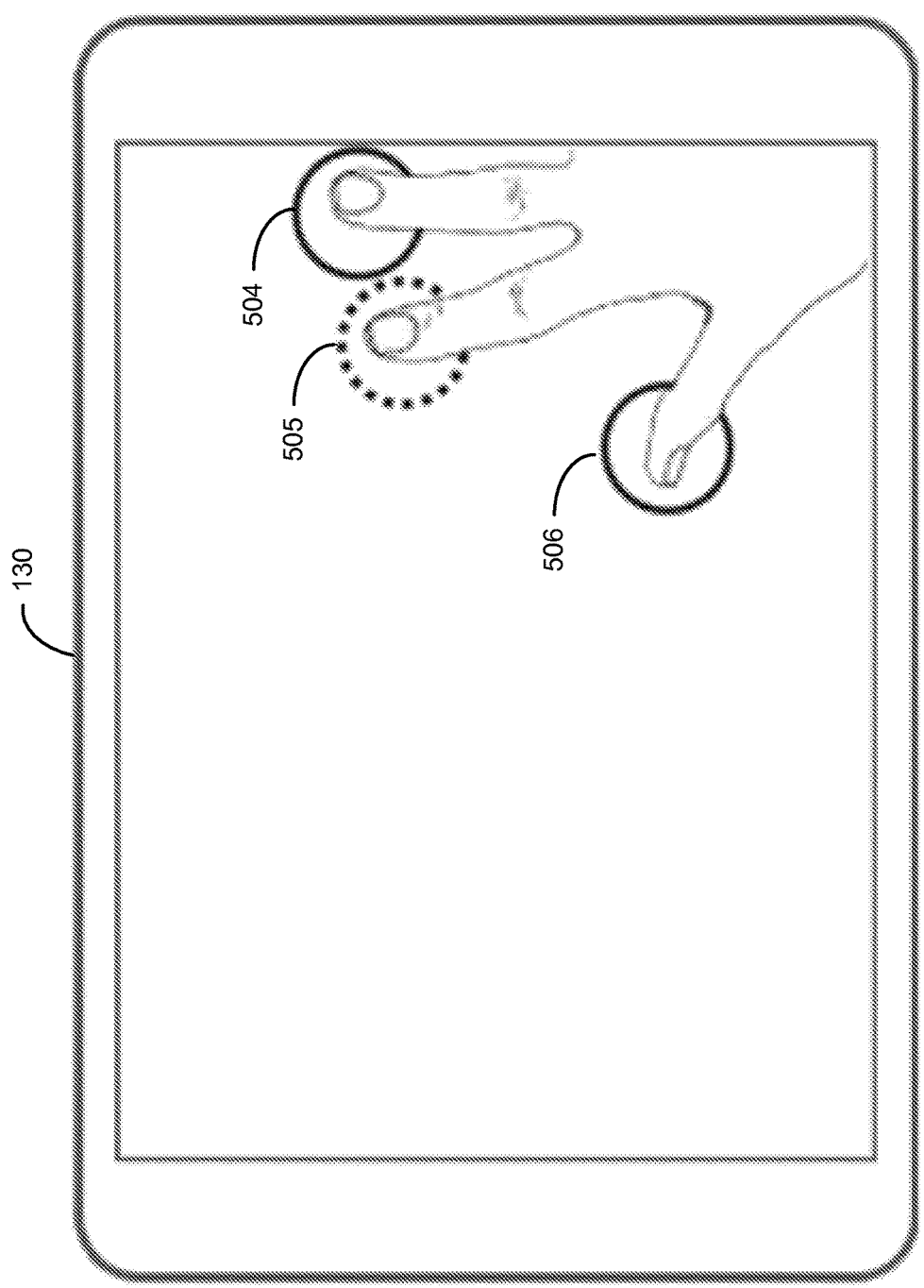

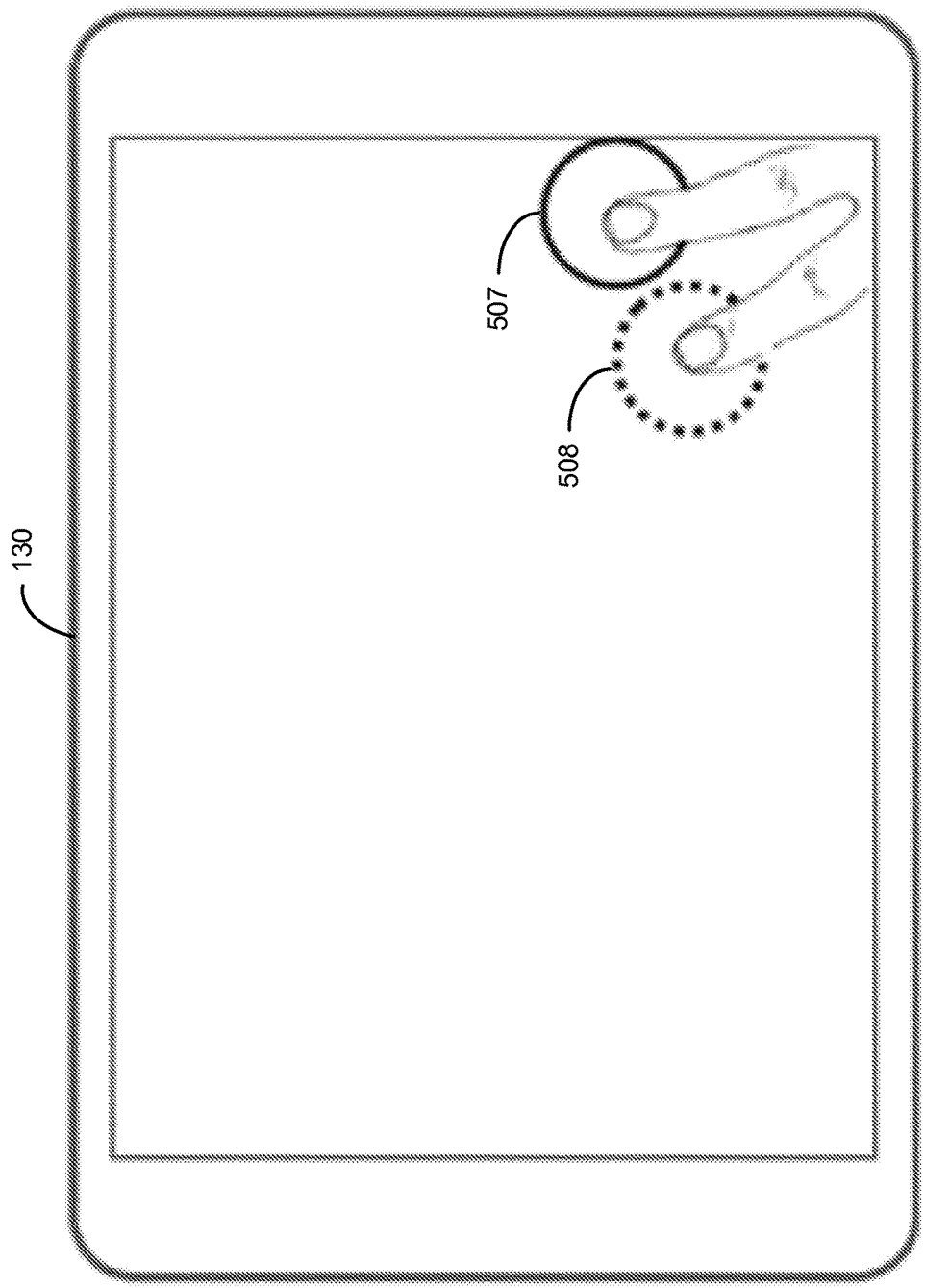

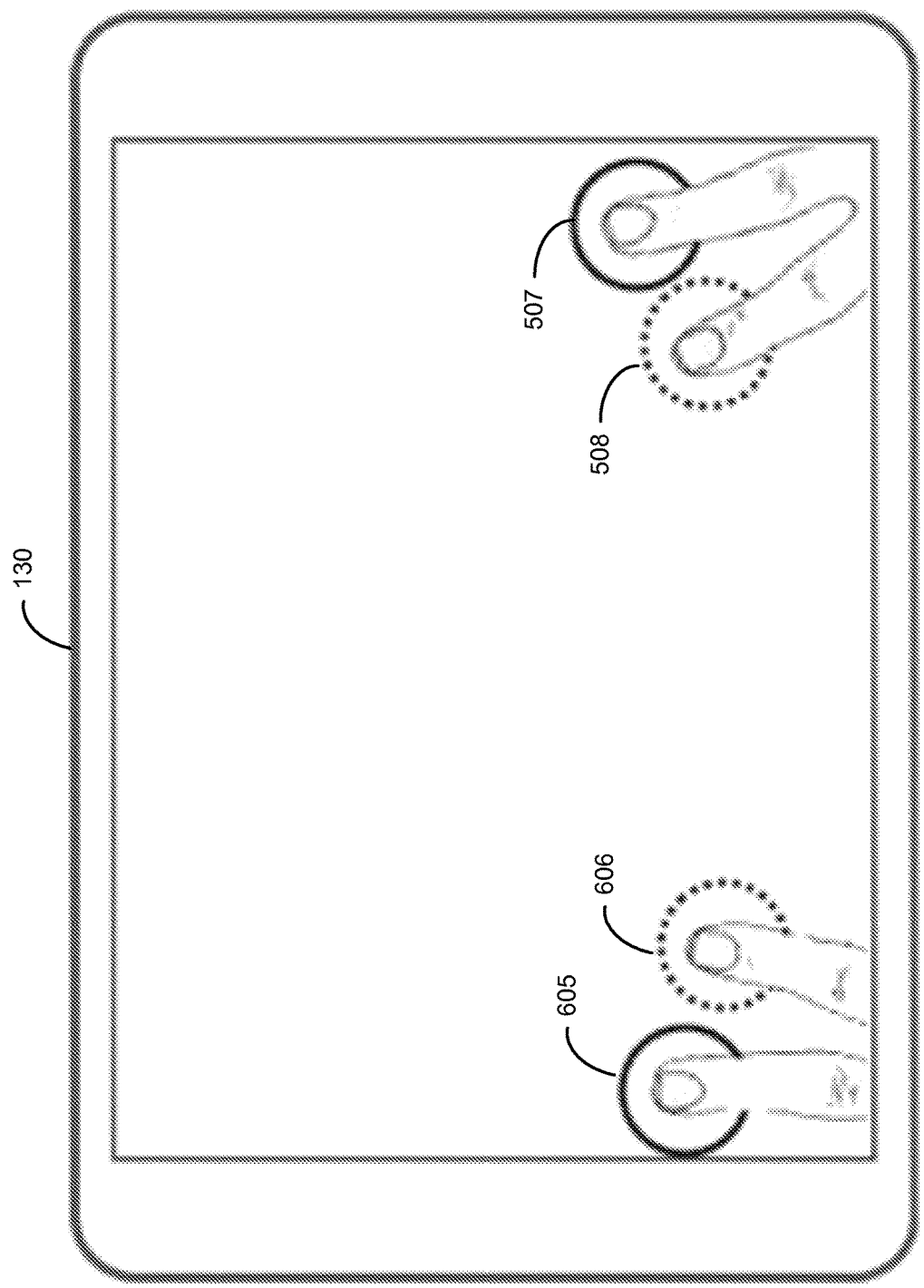

BIOMECHANICAL MOTION MEASUREMENT AND ANALYSIS FOR SELF-ADMINISTERED TESTS

CROSS-REFERENCE TO RELATED APPLICATION

This application claims priority under 35 U.S.C. § 119(e) to U.S. Provisional Patent Application Ser. No. 62/062,988, "Method and system for the collection of reliable biomechanical motion data via self-administered touchscreen data capture," filed Oct. 13, 2014, which is incorporated herein by reference in its entirety.

BACKGROUND

1. Field of the Disclosure

The present invention relates to systems and methods for biomechanical testing, and more specifically for a system and method for restricting user motions to ensure reliability of biomechanical data.

2. Description of the Related Art

More than 90 million American suffer from a brain disorder that affects their daily functioning. These disorders can be psychological, emotional, motor, cognitive or social in nature. Neuropsychological and neurological testing to identify such disorders is generally performed by a mental health professional to measure a person's cognitive functions, such as memory function, language function, decision making, organization, attention span, reasoning, intellectual capacity, learning or any other brain related functions or disorders as well as motor, social, mood or emotional issues. Traditionally, neuropsychological tests are typically administered in-person using a pencil and paper or otherwise manual format. A candidate is placed in a quiet environment with a clinician and must answer a questionnaire on paper or perform some activity, which is observed and scored by the clinician. Since the traditional format for neuropsychological testing requires a highly skilled clinician, the costs of such testing are significant. In addition, in the United States there is approximately one neuropsychologist per 25,000 patients and one neurologist for every 35,000 patients, and a result, there is an insufficient number of skilled clinicians available to provide these tests to those who may suffer from some type of neurological deficit.

Accordingly, there is an interest in providing computer-mediated tests of neurological, cognitive and motor skills that can be self-administered by users. However, users, either intentionally or unintentionally, use compensatory strategies in an attempt to improve performance in the completion of such test, thereby resulting invalid or incorrect results.

SUMMARY

Systems and methods are disclosed for collection of reliable biomechanical data via self-administered cognitive tests. A test administration module on a touch-sensitive device, such as a device having a touchscreen, is configured to execute a self-administered computer-mediated test. The test administration module configures a user interface for the device. The user interface comprises at least one motion restriction region and at least one testing region on the touch-sensitive surface, such as the touchscreen. The motion restriction region is configured to isolate specific biomechanical motion of interest to clinicians providing the self-administered test to the user, and further to prevent or reduce spurious motions from being performed by the user during the computer mediated test. In typical embodiments, this is accomplished by requiring the user to anchor a digit of his/her hands to each configured motion restriction region. The testing regions are configured to receive a touch input performed by a user using a specific digit. A touch input can include placing a specific finger on the touchscreen, lifting the finger from the touchscreen, or moving the finger while it is in contact with the touchscreen. The placement of the user's digits on the motion restriction region biomechanically isolates the specific digit by restricting the degrees of mechanical freedom by which the user's other fingers, as well as wrist, arm, elbow and shoulder can be moved or generate the muscle movements that can alter the physical movement of the specific finger. By so isolating a finger, the received inputs and associated measurements are more strictly correlated to specific areas of the cortex, and thus can be used to better identify potential cognitive deficits.

A user performs one or more touch inputs in accordance with instructions provided by the test administration module. For example, a test may require the user tap a specific her finger(s) in a testing region, for a specified period of time, or to trace a line between displayed objects. The motion data can be expressed as a series of touch events, and includes information describing the location of the touch event, the type of touch event, and the time at which the touch event occurred. The test administration module analyzes the recorded motion data to determine if the user successfully completed the self-administered test. Determination of successful completion involves detection and/or identification of one or more spurious touch inputs and identification of prohibited motions (e.g., lift-off or motion of a finger) in the motion restriction regions indicating that the user did not maintain contact with such regions during the test. These spurious touch inputs include actions performed by the user in an attempt to compensate for biomechanical deficits of the user, as well as actions performed inadvertently by the user which are indicative of biomechanical deficits. Detection of such spurious touch inputs, as well detection of prohibited motions, results in identification of potentially invalid test inputs in the testing region.

The features and advantages described in the specification are not all inclusive and, in particular, many additional features and advantages will be apparent to one of ordinary skill in the art in view of the drawings and specification. Moreover, it should be noted that the language used in the specification has been principally selected for readability and instructional purposes, and may not have been selected to delineate or circumscribe the inventive subject matter.

BRIEF DESCRIPTION OF THE DRAWINGS

The teachings of the present disclosure can be readily understood by considering the following detailed description in conjunction with the accompanying drawings.

Figure (FIG. 1 is a high-level block diagram illustrating an example environment for providing testing, according to one embodiment.

FIG. 4 is a table depicting an example record of motion data, according to one embodiment.

FIG. 5B illustrates an example user interface for conducting self-administered tests, according to one embodiment.

FIG. 5C illustrates an example user interface for conducting self-administered tests, according to one embodiment.

FIG. 6C illustrates an example user interface for conducting self-administered tests, according to one embodiment.

DETAILED DESCRIPTION

The Figures (FIG.) and the following description relate to various embodiments by way of illustration only. It should be noted that from the following discussion, alternative embodiments of the structures and methods disclosed herein will be readily recognized as viable alternatives that may be employed without departing from the principles discussed herein. Reference will now be made in detail to several embodiments, examples of which are illustrated in the accompanying figures. It is noted that wherever practicable similar or like reference numbers may be used in the figures and may indicate similar or like functionality.

In various embodiments, a client device is configured with a test administration application for conducting self-administered tests. The user interface of the test administration application includes motion restriction regions for restricting certain body parts from moving or certain body motions during the entire or particular segments of self-administered tests. For example, motion restriction regions are provided to anchor fingers from one or both hands to the touchscreen of the client device during self-administered tests. Accordingly, only target response motions in a test are captured and analyzed. Undesired motions that may interfere with assessment of users' cognitive and/or motor skills are reduced or excluded.

Figure 1:
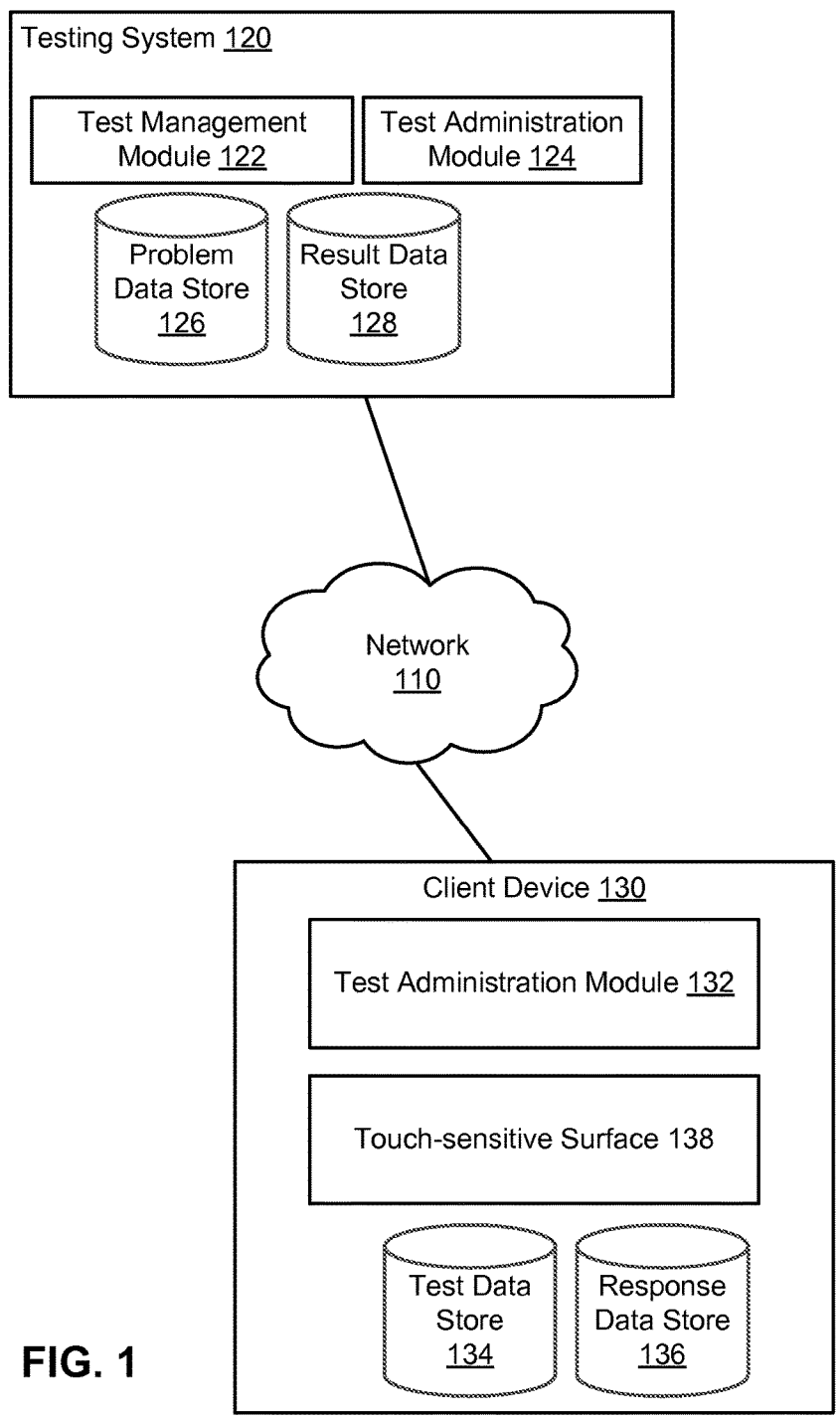

FIG. 1 is a high-level block diagram illustrating an environment 100 for providing testing, according to one embodiment. As shown, the environment 100 includes a network 110, a testing system 120, and a client device 130. The testing system 120 provides self-administered tests to users over a network 110 via client devices 130, and is one means of providing self-administered tests. While one testing system 120 and one client device 130 are shown in the example depicted in FIG. 1 for clarity, other embodiments may include different numbers of testing system and client devices.

The network 110 represents the communication pathway between the testing system 120 and the client device 130, and is one means of connecting the two devices. In one embodiment, the network 110 uses standard wireless and wired communications technologies and protocols and can include the Internet and associated protocols. In another embodiment, the entities on the network 110 can use custom and/or dedicated data communications technologies.

The testing system 120 comprises a test management module 122, a test administration module 124, a test data store 126, and a result data store 128, and is one means of maintaining and providing tests to users. The test management module 122 is one means for performing the function of creating and managing tests that are designed to assess one or more cognitive capabilities (e.g., intelligence, learning ability, reasoning aptitude, cognitive development, memory, etc.) and/or motor skills (e.g., coordination of a certain group of muscle movement, synchronization of hands and fingers,) of a user. Tests can be tasks that require the users' to respond by completing the tasks using physical inputs to the client device, such as touches, taps, drags, using one or more fingers. A user's input response is measured and analyzed to assess the user's cognitive aptitude and/or motor skills in completing the task. For example, a test may involve manipulating graphical representations of objects such as blocks or icons, or memorization of sequences of presented stimuli to test cognitive skills, or a combination thereof The test management module 122 allows an authorized user such as a clinician to create and configure a test such as configuring attributes associated with the test. A test may also include a set of instructions prompts informing the user how to take the test, required responses, response analysis criteria, and the like. The test data store 126 stores tests and associated attributes.

The test administration module 124 is one means for performing the function of managing, delivering, and conducting self-administered tests. A self-administered test includes a series of tasks and is designed to assess one or more cognitive capabilities and/or motor skills of a user. The test administration module 124 selects a set of tests stored in the test data store 126 and/or orders the selected tests. The tests may be selected and/or ordered according to a predetermined plan or randomly. The test administration module 124 provides visual or audible instructions to the user on how to take a self-administered test, presents the tests on the client device via the presentation of graphical objects, images, symbols or the like, then receives the user inputs on the client devices in response to the test. Users' test results including the measurement and analysis of the users' performance are stored in the result data store 128.

A client device 130 is a computing device that includes a touch-sensitive surface 138, such as a touchscreen, or touchpad, and is one means for enabling a user to access the testing system 120 and/or to receive testing service provided by the testing system 120. A client device includes hardware and software modules to provide self-administered tests, to receive user input, and to connect to the network 110 (e.g., via Wi-Fi, Long-Term Evolution (LTE) or other wireless communication protocols). In one example provided throughout the description, the client device 130 is a tablet or smartphone including a touchscreen with operating systems such as ANDROID or APPLE IOS. The touchscreen can be used as both input and output interfaces. The term "module" refers to computer program logic utilized to provide the specified functionality upon execution by the client device 130. Other embodiments of a computing device or a client device 130 can have different and/or other modules than the ones described here, and that the functionalities can be distributed among the modules in a different manner.

The user may access the testing system 120 and/or to receive testing service provided by the testing system 120 in a variety of ways. In some embodiments, a user may download and install a client application of the testing system 120 on the client device 130.

Client Device

Figure 2A:
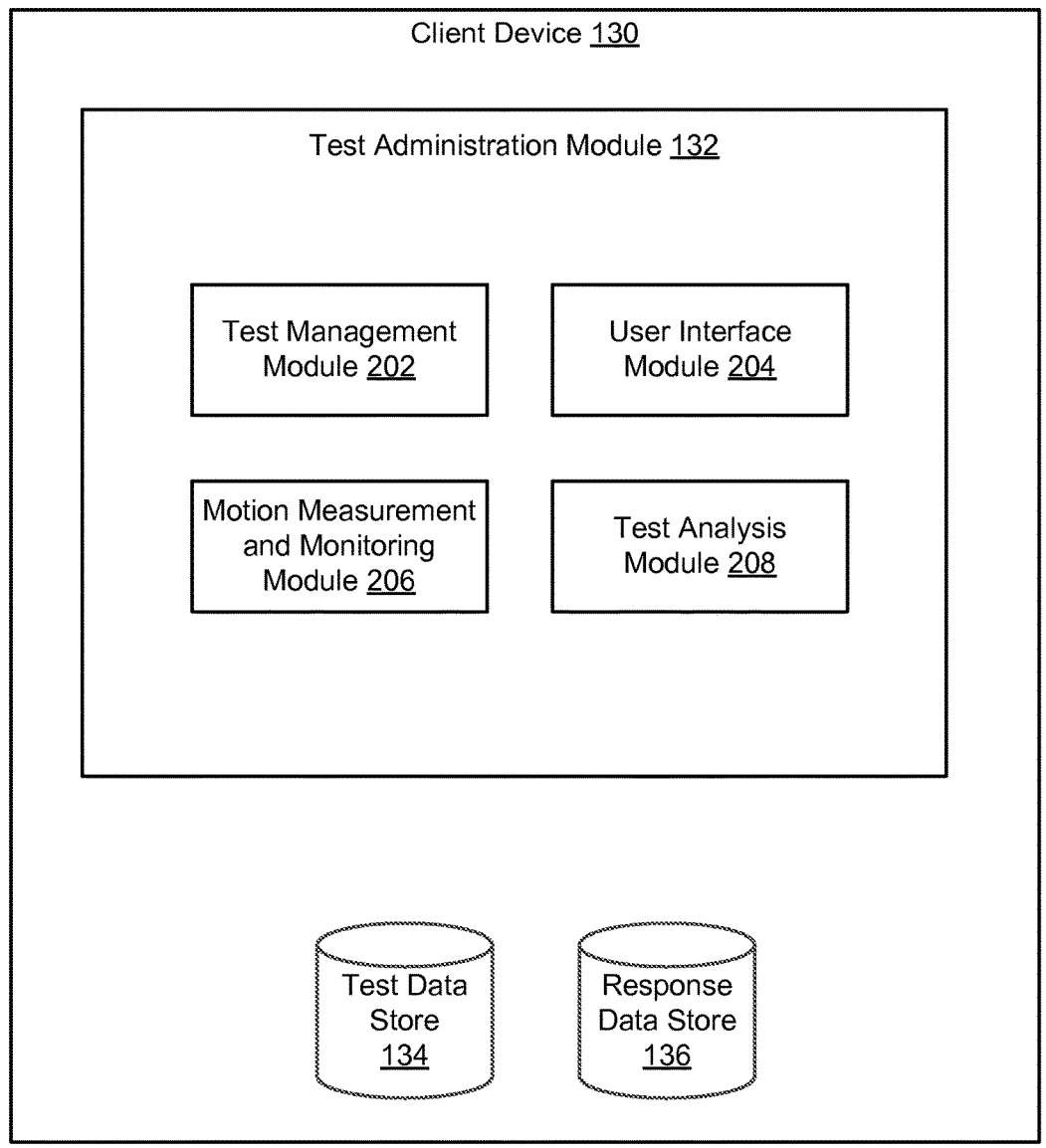
FIG. 2A is a block diagram of an example client device, according to one embodiment.

FIG. 2A is a block diagram of a client device 130, according to one embodiment. The client device 130 comprises a touch-sensitive surface 138, such as a touchscreen, touchpad, or the like, a test administration module 132, a test data store, and a response data store 136. As described in connection with FIG. 1, the test administration module 124 manages, delivers, and conducts self-administered tests. The test administration module 124 allows a user to take a self-administered test. The user provides inputs to the test via the touch-sensitive surface.

The test data store 134 is one means for storing various tests that can be taken by a user. Each test stored in the test data store 134 is associated with an instruction (e.g., text, media items such as images, video clips, sound tracks, etc.) to users. The response data store 136 is one means for storing the measurement of a user's response to tests.

The test administration module 132 is one means for performing the function of administering tests, and comprises a test management module 202, a user interface module 204, a motion measurement and monitoring module 206, and an optional test analysis module 208. The test management module 202 is one means for configuring tests for presentation to a user and then administers the tests to the user. The test management module 202 may select a set of tests based on the user's test request.

The test management module 202 configures the presentation of a test to ensure the test accurately and reliably assesses the user's biomechanical skills. Users may attempt to use compensatory strategies to improve their performance, either intentionally or unintentionally. For example, when a user is asked to perform a motion task, the user may perform an action within a testing region of the touchscreen using a portion of his/her body that is intended to remain stationary. Or, a user may provide additional inputs to the device using additional fingers. The test management module 202 configures a test such that users are prevented from using these and other compensatory strategies may result in invalid responses that do not reflect actual the actual cognitive or motor skills being tests, and thus the module 202 ensures that a user's response to the test is valid and reliable.

The test management module 202 configures a user interface associated with a test to include one or more motion restriction regions and one or more testing regions on the touch-sensitive surface 138 for conducting the test. Motion restriction regions are locations on the touch-sensitive surface 138, such as a touchscreen of the client device, to which one or more digits of the user must be anchored to (e.g., maintain substantially constant contact with one or more fingers of one or both hands) during the test. While the user's digits are anchored to motion restriction region and the particular body part is being constrained, the user provides touch inputs as responses to the test using a specific non-constrained body part (e.g., using other fingers of one or both hands that are free) within a testing region. The anchoring action serves to constrain the movement of a user's body part (e.g., finger, hand, wrist, elbow, shoulder, etc.), thereby limiting the degrees of freedom of the body parts and reducing the influence or contribution of any movement or muscular activity that such body parts may create. The constraint on the motion of particular body part(s) further ensures that the user has not employed any compensatory strategies (intentionally or unintentionally), and thus the actual input on the touch-sensitive surface 138 is valid inputs for the specific digit under test. For example, ensuring that all but one of the digits of a user's hand are in contact with motion restriction regions during the test ensure that the user is forced to perform a required task using a particular motion involving a particular finger. For purposes of convenience, in the following descriptions, the touch-sensitive surface is a touchscreen of the client device.

As one example, a motion restriction region is a predefined anchoring region (e.g., a circle with a center and a radius) displayed on the touchscreen of the client device. The anchoring region requires one or more of the user's fingers to be anchored within a defined area on the touchscreen of the client device during the administration of the test. That is, once the user's finger contacts an area of the touchscreen in the circle, the user's finger is registered to that particular area and required to maintain substantially constant contact with the particular area of the touchscreen during the test. In one embodiment, contact with the motion restriction region for at least 90% of the running test time is sufficient to be substantially constant contact (e.g., at least 0.9 s of the first 1.0 s of the test, 1.8 s of the first 2.0 s, 2.7 s of the first 3.0 s, and so forth). As such, the user's finger is prevented from moving away from the particular area of the touchscreen. The user's other body parts such as other fingers, shoulders, wrists, or elbows may also be prevented from moving by this motion restriction region even though they are not making contact with the client device as their movement will cause the user's finger to move off of the anchoring region during the test; thus the anchoring regions reduce the degrees for freedom of motion from the other body parts, and any contribution to the required motion inputs from the digit under test. If the user's finger loses contact with the anchoring region during the test, the test can be started over, or inputs received from the user in the testing region, while the contact with the anchoring regions is broken are indicated as being invalid.

The test management module 202 may configure one or more motion restriction regions included in the user interface associated with the test. The test management module 202 configures the motion restriction regions (e.g., a location, a time period, a size, permitted motions, prohibited motions, instructions, a distance from another motion restriction region, etc.) as defined in the test. For example, for a test that requires fine control of particular muscles, the test management module 202 configures the motion restriction regions as defined in the test to arrange the user's fingers into predetermined positions such that the user's control of the particular muscles can be assessed by restricting the motion of fingers that are not being test.

As some tests do not require inputs from both hands or all ten fingers, the test management module 202 configures one or more motion restriction regions to prevent interference or performance enhancement from the use of the free hand or finger. For example, when a test requires a user to use her left hand, the test management module 202 may configure one or more motion restriction regions to anchor the user's right hand to the client device, thereby preventing the user from providing inputs with the right hand. For example, when a test specifies a user to use the index finger of her non-dominant hand (the digit under test) to perform pivoted finger tapping, the test management module 202 can configure six motion restriction regions on the touchscreen of the device: four to anchor the user's thumb, ring, middle, and pinky fingers of the non-dominant hand, and two to anchor the user's thumb and middle finger of the dominant hand, thereby effectively ensuring that only the non-dominant index finger can provide inputs during the test. The anchoring of the digits of the non-dominant hand biomechanically isolates the index finger (or which is the digit under test). The test management module 202 configures the four motion restriction regions separated by a distance such that the four fingers are anchored in a substantially natural way, leaving a remaining finger on the non-dominant hand free to provide the required tapping inputs. The test management module 202 configures the two remaining motion restriction regions separated from the other four motion restriction regions such that the user cannot use the other fingers of her dominant hand to aid tapping. This is just one example of how motion restriction regions may be used; other examples are described below.

The test management module 202 may configure a user interface associated with a test that includes one or more testing regions on the touchscreen. A testing region is a region on the touchscreen configured to receive target responses from the user. The test management module 202 configures the testing region(s) (e.g., a location, a time period, a size, permitted motions, prohibited motions, instructions, a distance from another motion restriction region, etc.) as defined in the test. For example in a finger tapping test of the non-dominant hand, the user is required to tap the index finger of her left hand within the testing region. Tapping the index finger outside the testing region is an invalid response. The test management module 202 thus displays a testing region according on the display in which to receive the finger taps, and then one or more anchoring regions to receive touches from fingers from one or both hands.

There are various different arrangements of motions restriction regions that may be used. In one embodiment, the test management module 202 configures the user interface to include motion restriction regions for anchoring a user's thumb and any three fingers of index, middle, ring, and pinky fingers of the right or left hand. The user interface is configured to include a testing region for the other finger that is not restricted (e.g., index, middle, ring, or pinky). The motion restriction regions and the testing region each are a circle. The centers and radius of the circles as well as the distance between the circles are configured such that the user's hand and fingers are positioned substantially naturally and comfortably when five fingers being positioned in the respective motion restriction region or testing region.

Other embodiments provide the following combinations of motion restriction regions:
1) third finger and thumb anchored on tested hand and three anchored digits on opposing hand;
2) third finger and thumb anchored on tested hand and two anchored digits on opposing hand;
3) third finger and thumb anchored on tested hand and one anchored digit on opposing hand;
4) three fingers anchored with thumb unanchored on tested hand and two anchored digits on opposing hand;
5) three fingers anchored with thumb unanchored on tested hand and three anchored digits on opposing hand;
6) third finger anchored on tested hand and two anchored digits on opposing hand; or
7) third finger anchored on tested hand and three anchored digits on opposing hand.

The test management module 202 configures the user interface for conducting the tests to ensure that instructions associated with a test, motion restriction regions, and/or testing regions are accurately presented to the user. The instructions associated with a test, a test, a motion restriction region, or testing region provide information to a user to enable the user to understand and respond to the test and the test in a controlled manner such that the user's response meets the motion requirement. For instance, display attributes such as the font, volume, color, and the like of user interface elements are configured to ensure that instructions associated with a test, motion restriction regions, and/or testing regions are displayed to a user. Instructions can be visual or auditory.

The user interface module 204 is one means for presenting the user interface as configured by the test management module 202 for conducting a test. The user interface module 204 presents various user interface elements, motion restriction regions, testing regions, or instructions associated with the test, test, motion restriction region, or testing region visually or auditorily. For example, the user interface module 204 renders and presents visual objects such as texts or graphics, auditory signals such as speech or music. For example, graphics include text, web pages, icons including user-interface objects including soft keys, digital images, videos, animations, and the like. The user interface module 204 may include computer executable instructions to enable users to respond to a test or test or comply with motion restriction requirement. For example, the user may identify and select regions, portions, locations, or user interface elements presented on the display screen.

In some embodiments, the test management module 202 may configure the user interface dynamically, for example, based on the user's response. The user's response may be detected by the motion measurement and monitoring module 206. For instance, upon detecting that a user is partially following instructions, the test management module 202 configures the user interface to include the instructions that need to be followed by the user. Continuing with the example of the test requiring the user to use her non-dominant hand to perform pivoted finger tapping for example, the user has anchored her index, middle, and pinky fingers but has not anchored the thumb of the non-dominant hand. The test management module 202 may configure the user interface to highlight the motion restriction region for anchoring the user's thumb of the non-dominant hand.

The motion measurement and monitoring module 206 is one means for detecting a motion input by a user on touchscreen of the client device 130. The touch-sensitive surface 138 of the client device 130 supports multi-touch motions. Different motions have different touch patterns. A touch pattern is characterized by one or more touch points and their associated movements, from which the spatial or geometrical relationships between the touch points can be determined.

To start the test, test management module 202 presents instructions to the user to place certain digits in the motion restricted regions. The motion measurement and monitoring module 206 detects motion inputs on the touch-sensitive surface and determines that the user has placed the digits accordingly. At this point the test management module 202 initiates the testing, for which the user provided inputs with the digit under test to the testing region. The motion measurement and monitoring module 206 detects these inputs, as well as any inputs in the motion restriction regions. The motion measurement and monitoring module 206 may use the touch event data to generate motion data to measure a user's motion when a motion is detected and store the motion data in the response data store 136. In some embodiments, motion data includes motion events as well as the time, locations, and types (e.g., restricted, test, free) of the motion events. The motion measurement and monitoring module 206 compares the location of a motion event to a location of a motion restriction region or of a testing region to determine the type of a motion event. A motion event is restricted when its location is within a motion restriction region, test when its location is within a testing region, or free when its location is neither within a motion restriction region nor within a testing region.

In some embodiments, the motion measurement and monitoring module 206 receives from the underlying operating system motion events including a finger-down event, a finger-up event, and a finger-move event. A finger-down event indicates an initial touch of a position (e.g., a horizontal position and a vertical position) on the touchscreen of the client device 130. A finger-up event indicates the finger is no longer touching the touch screen at substantially the same position as the finger-down event, and thus may no longer be anchored to the motion restriction region. A finger-move event indicates the finger moves away from the position associated with the finger-down event. A motion event is associated with a time stamp indicating the time of the event.

The motion measurement and monitoring module 206 monitors the user's response to validate whether a user responds in a controlled manner. A user's response is monitored and validated to ensure that user is following the instructions and responding as required by the test. For example, the motion measurement and monitoring module 206 monitors the user's motion in a motion restriction region to determine whether the user's digits are maintained anchored to the motion restriction region, while the digit under test provides inputs to the testing region. As one example, the motion measurement and monitoring module 206 determines from the motion data whether a user anchors the user's digits to the motion restriction regions when the user is required to mimic a tapping pattern with his/her index finger (digit under test), by detecting whether any of the user's other fingers have lifted off of the motion restriction regions or moved out of these regions, in which case the test may be terminated (or restarted) or the user's response to the test is considered as invalid and discarded.

In some embodiments, the motion measurement and monitoring module 206 monitors the user's response by evaluating and analyzing the motion data generated. For example, restricted motion events are compared to identify a user's movement in the motion restriction region and the identified movement is compared to the movements permitted or prohibited in the motion restriction region. When the motion measurement and monitoring module 206 detects that the user's movement in the motion restriction region is not permitted or prohibited, the user's response is determined as invalid. Generally, during a test, a finger-up event in a motion restriction region, or movement out of the boundaries of a motion restriction region is prohibited.

When the motion measurement and monitoring module 206 determines that the user is not responding as permitted by the test, the test administration module 132 may conduct the test in a variety of ways. In some embodiments, the test administration module 132 may terminate or restart the test. Alternatively, the test management module 202 alerts the user that he or she has violated the test requirement and continues administering the test. The test management module 202 may determine that the data point received at the time of the prohibited motion event fails to comply with the test requirement is invalid and discard the data point. In some embodiments, the motion measurement and monitoring module 206 may associate the motion data with a record that the user failed to constrain his or her movement without terminating the test. The motion data with the record can be analyzed along with other generated motion data.

The test analysis module 208 is one means for evaluating a user's performance in the test. The test analysis module 208 may analyze the motion data collected by the motion measurement and monitoring module 206 during the test to evaluate the user's performance. The test analysis module 208 may analyze a user's response to each task included in the test to determine the user's performance in the test as an aggregation of all the tasks of the test. The user's response to each task included in the test may be evaluated by using the required response and/or evaluation criteria associated with the test. The test analysis module may store a user's performance on each test in the response data store 136.

Method of Conducting a Self-Administered Test

Figure 2B:
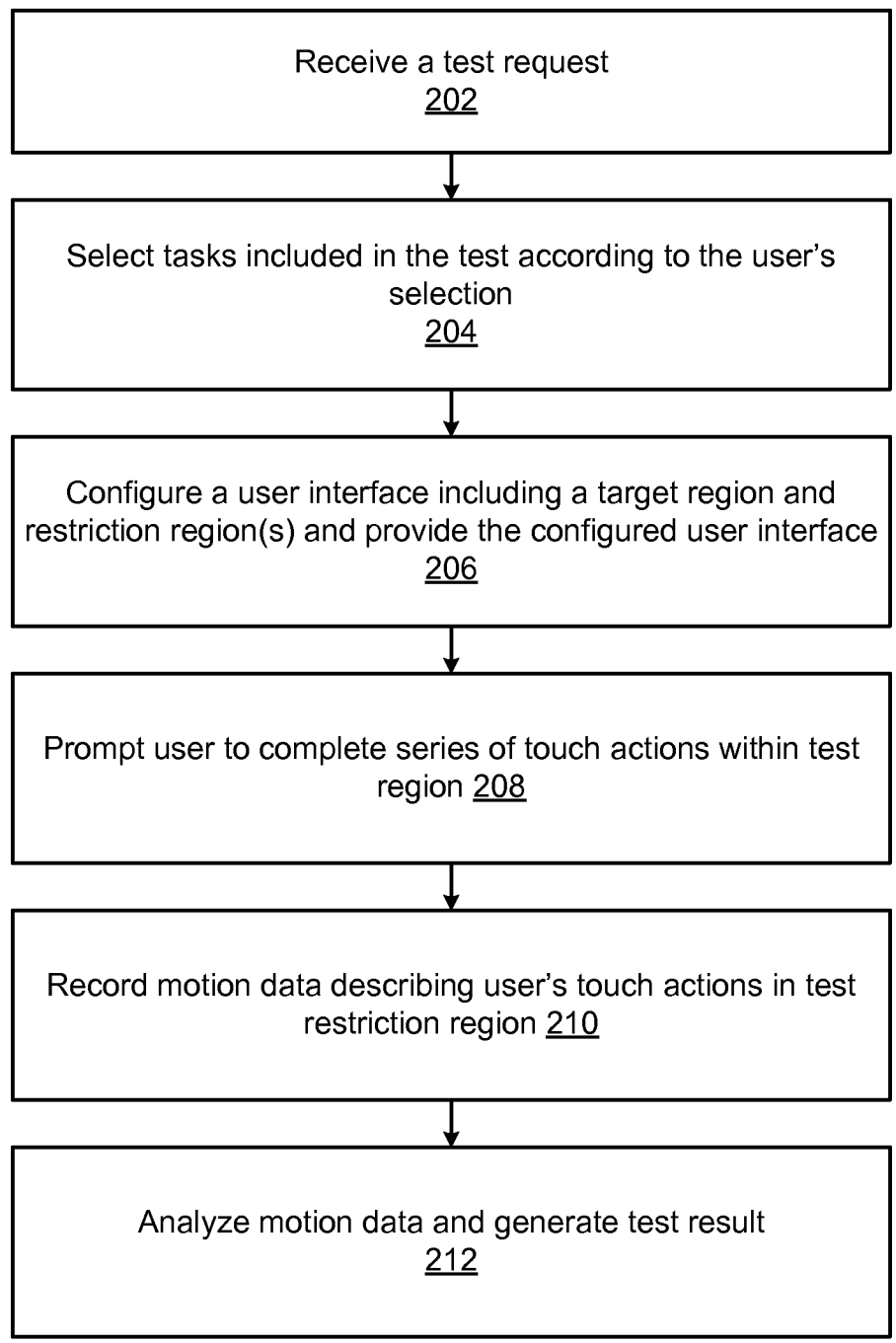
FIG. 2B is a flow diagram of an example method of collection biomechanical motion data based on a self-administered test, according to one embodiment.

FIG. 2B is a flow diagram illustrating an example method of conducting a self-administered test, according to one embodiment. The test administration module 132 receives 202 a test request from a user. A self-administered test (or a test) includes a series of problems and is designed with one or more objectives to assess one or more cognitive capabilities and/or motor skills of a user. The test administration module 132 selects 204 the test according to the input of the user. For example, the test administration module 132 identifies one or more objectives associated with the requested test and selects problems based on the identified test objectives. The test administration module 132 configures how the test should be conducted such that a user's cognitive and/or motor skills can be assessed accurately and reliably.

The test administration module 132 configures 206 a user interface to include at least one testing region and one motion restriction region and presents the user interface as configured. A testing region and associated instructions prompt a user to perform one or more touch inputs within the bounds of the region. Actions are typically performed using a finger of one hand, which is the digit under test. The specific digit may be any of the digits (index, middle, third, ring, pinky, thumb). In common embodiments, the action required may include tapping, holding, or moving the finger on the display screen of the computing device. A motion restriction region and associated instructions constrain the movement of one or more body parts (e.g., finger, hand, wrist, elbow, shoulder, etc.). The test administration module 132 may configure one or more motion restriction regions included in the user interface associated with the problem or test. In some embodiments, the test administration module 132 determines various attributes (e.g., a location, a time period, a size, permitted motions, prohibited motions, a distance from another motion restriction region, etc.) of a motion restriction region according to one or more attributes associated with the task. The test administration module 132 configures the user interface for conducting the test or a task of the test to ensure that instructions associated with a test, a task, motion restriction regions, and/or testing regions are accurately presented to the user.

The test administration module 132 prompts 208 the user to first position one or more digits that are not under test (other digits) to multiple ones of the motion restriction regions. Once these digits are placed in contact, the test administration module 132 prompts the user complete a series of touch inputs in the testing region. The test administration module 132 than starts the test, and collects motion data from the touch inputs received on the touch-sensitive surface. In some embodiments, motion data includes motion events as well as time, locations, and types (e.g., restricted, test, free) of the motion events. The test administration module 132 monitors the motion data of the touch inputs to validate whether the touch inputs in the testing region are valid. In some embodiments, when a user's touch input is invalid, the test administration module 132 may note the user's input is invalid while still conducting the test. In some embodiments, when a user's touch input is invalid, the test administration module 132 may terminate the test. The test administration module 132 records 210 motion data describing the user's touch inputs.

Computer Diagram

Figure 3:
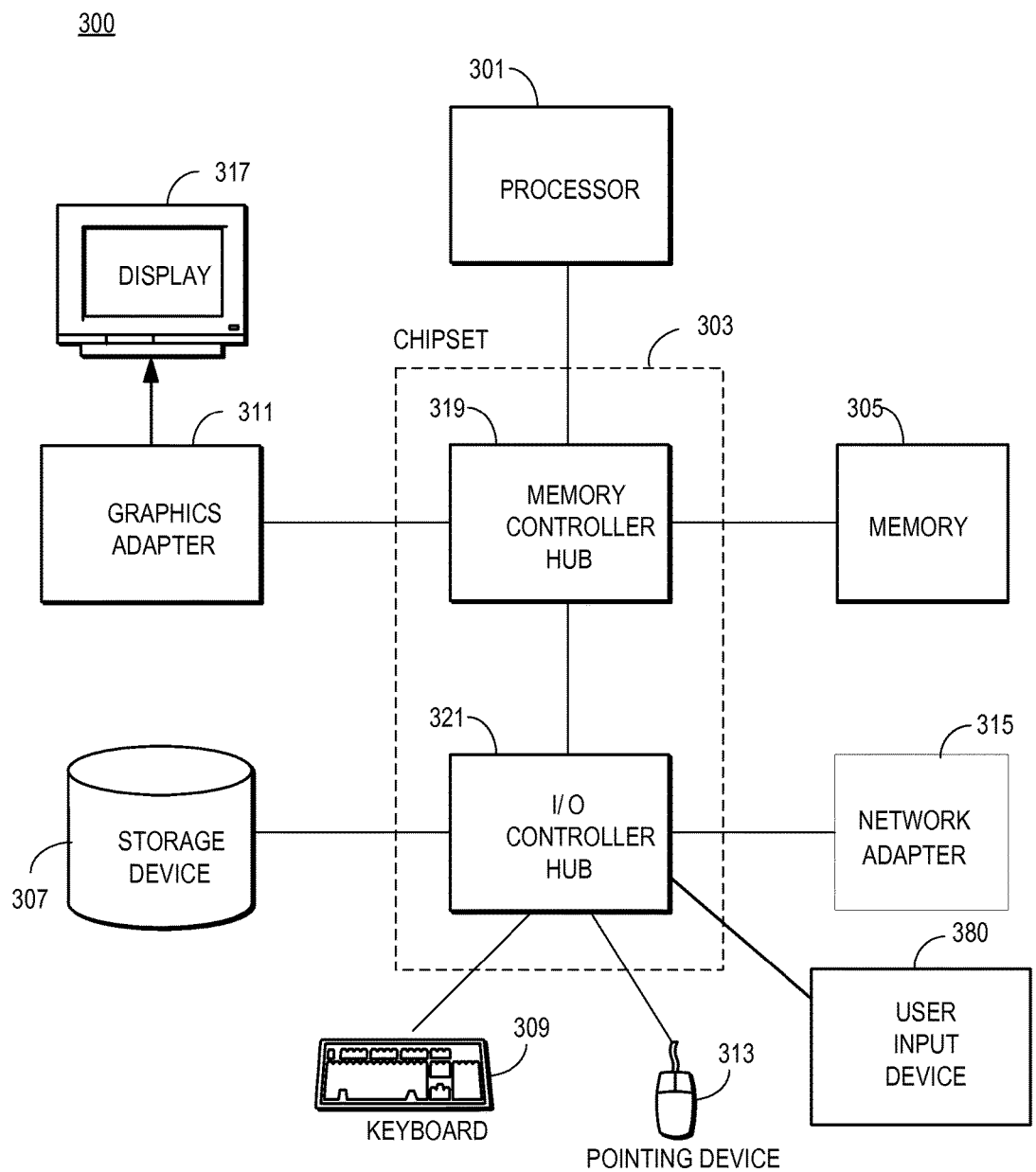
FIG. 3 is a high-level block diagram illustrating a typical computer for acting as a computing device, according to one embodiment.

FIG. 3 is a high-level block diagram of a computer 300 for example, for acting as a computing device according to some embodiments. Illustrated are at least one processor 301 coupled to a chipset 303. Also coupled to the chipset 303 are memory 305, a storage device 307, a keyboard 309, a graphics adapter 311, a pointing device 313, and a network adapter 315, and touch-sensitive surface 380. A display 317 is coupled to the graphics adapter 311. In one embodiment, the functionality of the chipset 303 is provided by a memory controller hub 319 and an I/O controller hub 321. In another embodiment, memory 305 is coupled directly to the processor 301 instead of the chipset 303.

The storage device 307 is any non-transitory computer-readable storage medium, such as a hard drive, compact disk read-only memory (CD-ROM), DVD, or a solid-state memory device. Memory 305 holds instructions and data used by the processor 301. The pointing device 313 may be a mouse, track ball, touch panel, or other type of pointing device, and is used in combination with the keyboard 309 to input data into the computer 300. The touch-sensitive surface 380 is configured to receive touch inputs (including multi-touch inputs). In some embodiments the touch-sensitive surface 380 may be integrated into the display 317, for example in a touchscreen. The graphics adapter 311 displays images and other information on the display 317. The network adapter 315 couples the computer 300 to a local or wide area network (e.g., the network 110 illustrated in FIG. 1).

As is known in the art, a computer 300 can have different and/or other components than those shown in FIG. 2A. In addition, the computer 300 can lack certain illustrated components. As is known in the art, the computer 300 is adapted to execute computer program modules for providing functionality previously described herein. In one embodiment, program modules are stored on the storage device 307, loaded into memory 305, and executed by the processor 301.

Example Motion Data

FIG. 4 is a table depicting an example record of motion data, as may be stored in the memory of the client device during the administration of a test, according to one embodiment. In some embodiments, this table may be produced by the motion measurement and monitoring module 206 during administering of a test to a user. The table 400 features a sequence of touch events, and each event is recorded as a separate row. The events are received from the underlying operating system as the user inputs are received on the touch sensitive surface, such as the touch screen. As noted above, each touch invention comprises data indicating a type of event, a location, and time of the event. The types of event include a finger-down (FD) events, finger-up (FU) events, and finger-move (FM) events. The module records these events, and analyzes them as they are received to determine which events are inputs to a testing region, inputs to a motion restriction region, or inputs to other areas.

In the example of FIG. 4, the first touch event occurs at a time $t_0$, when the user touches the touch sensitive surface at coordinates $(x_1, y_1)$. The module 206 determines whether this location is in a motion restriction region, a free area, or a testing region, and stores an indication of the same in the table. The module 206 identifies coordinate $(x_1, y_1)$ as located within the Restriction 1 region. In a typical embodiment, this first finger might be the user's thumb. The event is identified as finger-down (FD) event. Next, at a time $t_1$, the user places a second finger at coordinates $(x_2, y_2)$ which the module 206 identifies as being located in a second region, Restriction 2. Typically, Restriction 2 region might be located proximally to Restriction 1 region. This finger touch is also identified as an FD event. At a time $t_2$, the user places a third finger at coordinates $(x_3, y_3)$ which the module 206 identifies as being located in a third region, Free 1 (neither a testing region nor a restricted region). In one embodiment, this touch input could be performed by the user with his/her ring finger. This event is also identified as a FD event. Next, at time $t_3$, the user places a fourth finger at coordinates $(x_4, y_4)$ which the module 206 identifies as being located in a fourth region, Free 2 (neither a testing region nor a restricted region). In one embodiment, this touch input could be performed by the user with his/her little finger. This event is also identified as a FD event. Finally, at a time $t_4$, the user places a fifth finger at coordinates $(x_5, y_5)$ which the module 206 identifies as being located on a fifth region, Target 1. In one embodiment, this touch input could be performed by the user with his/her index finger. This event is identified as FD event.

It should be noted that the previously described sequence of finger events is merely illustrative, and in practice many different sequences of events could be received. For example, the user may place his/her index finger within the Target 1 region before he/she places any other fingers onto the touchscreen of the client device 130. The user could subsequently place the remaining fingers of his/her hand onto the screen, each finger touching a motion restriction region or a free region. In some embodiments, the motion measurement and monitoring module 206 may dynamically monitor touch events as they occur, and based on the available information, determine whether a finger is in contact with a particular region.

In the process of performing a touch input in response to prompts and/or directions communicated by the test administration module 132, the user may inadvertently perform spurious touch inputs. One such action might involve moving a finger within a restricted region instead of keeping it stationary as directed. The motion measurement and monitoring module 206 makes a record of these movements and includes them as part of the motion data. The module 206 may also include an indication in the motion data that the touch input was not permitted. Referring again to FIG. 4, at time $t_5$, the user moves his/her finger which was previously placed in region Restriction 1 at time $t_0$. This touch event is designated by the module 206 as a FM event. Later, at time $t_6$, the user moves his/her finger which was previously placed in region Restriction 2 at time $t_1$. This touch event is also designated as a FM event.

In some embodiments, the test analysis module 208 may be configured to analyze touch inputs reported by the motion measurement and monitoring module 206 and identify one or more of them as spurious or prohibited. The test analysis module 208 could further apply a threshold against spurious touch events. For example, if the number of identified invalid touch events is in excess of a threshold value, then the test analysis module 208 may determine that the user has failed the test. The threshold may be established by the test designer based on a determination of a desired minimum amount of valid inputs useful for diagnostic purposes.

Returning to FIG. 4, at time $t_7$, the user lifts his/her finger which was previously placed in region Target 1 at time $t_4$. This touch event is designated as a FU event by the motion measurement and monitoring module 206.

At time $t_8$, the user returns his/her finger to the region Target 1. the motion measurement and monitoring module 206 designates this as a FD event. Similar to the actions performed by the module 206 at time $t_7$, the module 206 again stores a record of this touch input.

In some embodiments, the test analysis module 208 may determine a level of reliability for biomechanical data collected by the motion measurement and monitoring module 206 based on an assessment of spurious or prohibited touch inputs. For example, a test taker with severe muscle dysfunction caused by a movement disorder might be unable to control his/her index finger in order to repeat a tapping pattern in a testing region. In an intentional or unintentional compensatory action, the test taker might pivot his elbow and/or wrist in order to contact the testing region with his index finger. In some embodiments, this compensatory action may cause the other five digits of his hand to move within their respective motion restriction regions. These movements, if of a sufficient magnitude, would trigger the motion measurement and monitoring module 206 to record one or more touch inputs as a FM or FU event in a motion restriction region. Subsequently, the test analysis module 208 may analyze these recorded touch inputs and determine that they are spurious. The test analysis module 208 could further determine a maximum threshold for spurious touch inputs. If the number of spurious touch inputs is in excess of the threshold, then the test analysis module 208 could indicate that the biomechanical data collected via the inputs to the testing region is unreliable. In other embodiments, the test analysis module could produce a quantitative estimate of reliability for the biomechanical data based on the number of spurious touch inputs identified. For example, the test analysis module may determine the percentage of valid test inputs based on the number (or amount of time) test inputs were received while no spurious motions were recorded in the motion restriction region relative to the total number of test inputs (or total test time).

It should be noted that the test administration module 132, and in particular the motion measurement and monitoring module 206, can be configured to modify, re-configure, or terminate the test at any time. Modification, re-configuration, or termination may occur in response to a number of conditions, such as recordation of an unacceptable number of spurious touch inputs.

Example User Interfaces

Figure 5A:
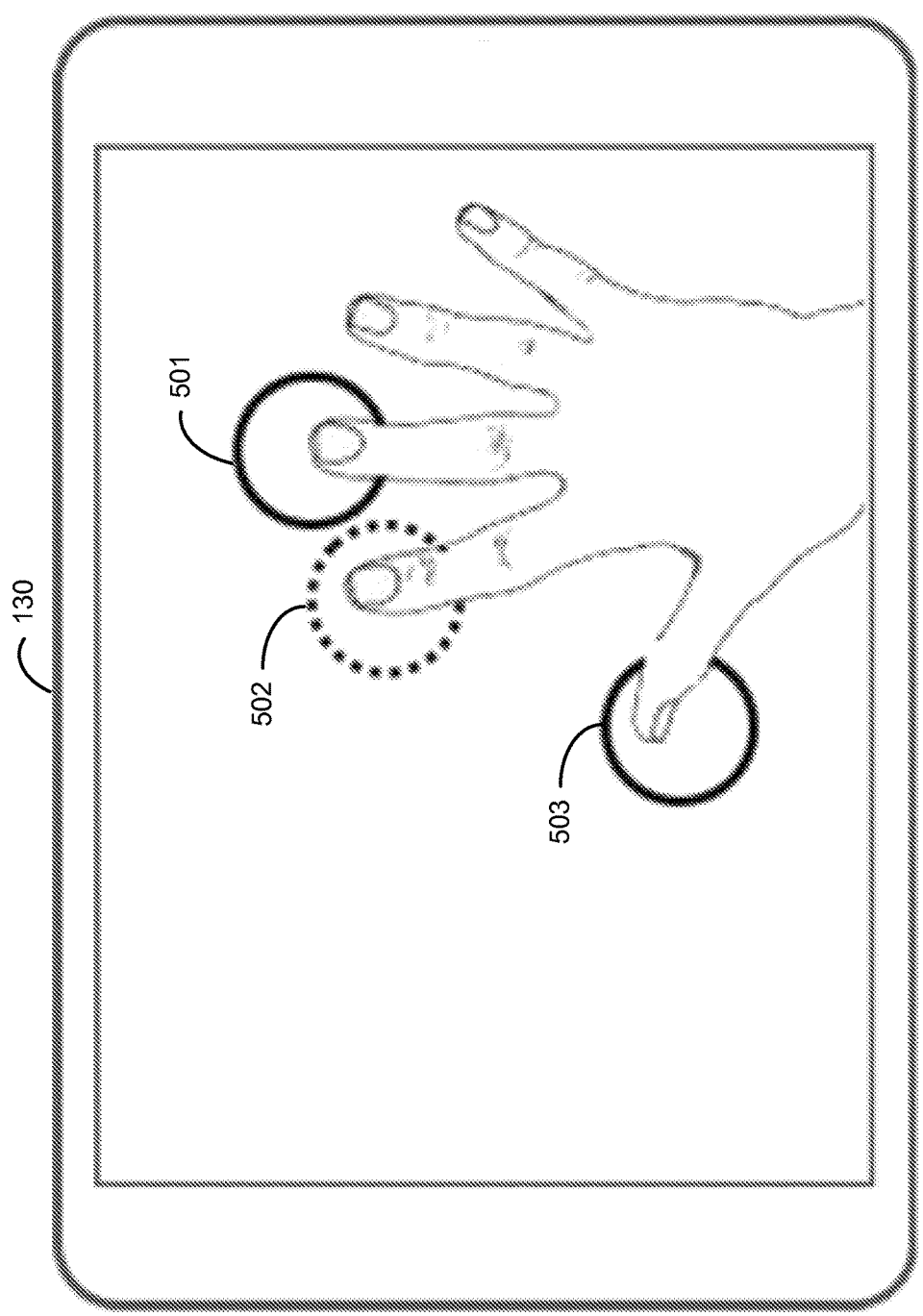
FIG. 5A illustrates an example user interface for conducting self-administered tests, according to one embodiment.

FIGS. 5A through 5C each illustrate an example user interface for conducting self-administered tests, according to one embodiment. The illustrated example user interface presented on the client device 130 in FIG. 5A includes motion restriction regions 501 and 503, and testing region 502. The motion restriction regions 501 and 503 are for anchoring a user's right middle finger and right thumb respectively. In addition, the centers of the motion restriction regions 501 and 503 are separated by an average distance between the tips of an adult's middle finger and thumb.

The testing region 502 is configured to receive a touch input performed by the index finger of the user's right hand. The configuration of motion restriction regions 501 and 503 is intended to ensure that any motion performed within testing region 502 is in fact performed by the index finger of the same hand. The ring finger and little finger of the right hand also contact the screen of the client device 130. However, these fingers do not make contact within either a restriction region or a testing region configured by the user interface module 204 of the test administration module 132.

Referring back to FIG. 4, the touch inputs listed in the table 400 are intended to describe an example user interface similar to that depicted in FIG. 5A. FIG. 5A depicts the entirety of a user's right hand being placed on the touchscreen of the client device 130. In typical embodiments, the user does not place his/her fingers onto the touchscreen at exactly the same time. Thus, the act of placing his/her hand on the touchscreen is actually a series of individual touch inputs, each one distinguishable by the motion measurement and monitoring module 206. For example, the user may place his/her thumb onto the touchscreen first. With reference to FIG. 4, this action constitutes a finger-down (FD) event, as previously described, and occurs at time $t_0$. Further, if the user places his/her thumb as directed, the identified region of the FD event is the motion restriction region Restriction 1. Likewise, the module 206 identifies each subsequent touch input, classifying each as a FD event, noting the time at which it occurs, and identifying the region affected (whether a restricted region, a testing region, or neither). In the embodiment of FIG. 5A, a user may be prompted to perform a tapping motion with his/her index finger in testing region 502. In this situation, a single tap action is decomposed by the motion measurement and monitoring module 206 as a finger-up (FU) and finger-down (FD) pair. Referring to FIG. 4, the module 206 observes that the user performs a FU action at time $t_7$ in testing region Target 1. The module 206 subsequently observes that the user performs a FD action at time $t_8$, also in region Target 1. The motion measurement and monitoring module 206, either alone or in conjunction with the test analysis module 208, identifies this series of touch inputs as the "tap" action which the user was asked to perform.

It should be noted that the test analysis module 208 may be configured to identify user actions composed of non-consecutive touch inputs. In one embodiment, the motion measurement and monitoring module 206 may identify a touch input performed at time $t_{7.5}$, occurring before the FU event at $t_7$ and the FD event at $t_8$. The touch input at time $t_{7.5}$ may be further identified by the module 206 as a touch input involving a finger-move (FM) of a finger within a motion restriction region (e.g. Restriction 2). Depending on one or more assessment parameters configured by the test management module 202, the test analysis module 208 may identify this touch input as spurious. The test analysis module 208 may subsequently disregard this spurious event or terminate the test.

Returning to FIGS. 5A-5C, the illustrated example user interface presented on the client device 130 in FIG. 5B includes motion restriction regions 504 and 506 and testing region 505. The motion restriction regions 504 and 506 anchor a user's middle finger and thumb of his/her right hand, respectively. In addition, the centers of the motion restriction regions 504 and 506 are separated by an average distance between the tips of an adult's thumb and middle fingers. Furthermore, the motion restriction regions 504 and 506 are positioned such that the user's right hand is anchored to the lower right corner of the client device 130. The testing region 505 is configured to receive a touch input performed by the index finger of the user's right hand. The configuration of motion restriction regions 504 and 506 is intended to ensure that any motion performed within testing region 505 is in fact performed by the index finger of the same hand. It should be noted that in the embodiment depicted in FIG. 5B, the user's right hand only partially contacts the client device 130. This differs from the embodiment depicted in FIG. 5A, wherein the user's entire right hand is in contact with the client device 130.

The illustrated example user interface presented on the client device 130 in FIG. 5C includes motion restriction region 507 and testing region 508. The motion restriction region 507 anchors a user's right middle finger. The testing region 508 is configured to receive a touch input performed by the user's right index finger. In addition, the centers of the motion restriction region 508 and the touch region 507 are separated by an average distance between the tips of an adult's middle and index fingers. Furthermore, the motion restriction region 508 and touch region 507 are positioned such that the user's right hand is anchored to the lower right corner of the client device 130 and the other fingers are prevented from touching the touchscreen of the client device 130.

The example user interfaces illustrated in FIGS. 5A through 5C require a user to anchor fingers from a single hand to the touchscreen of the client device 130 to prevent that hand from moving and also to prevent free (i.e., non-anchored) fingers from performing intentional or unintentional motions that obscure biomechanical deficits or otherwise degrade the reliability of biomechanical data received from the finger being tested. The motion restriction regions may be configured to anchor a user's fingers in a variety of arranged positions that are not necessarily symmetrical positions as illustrated. As such, non-anchored fingers are prevented from participating in compensatory actions.

Figure 6A:
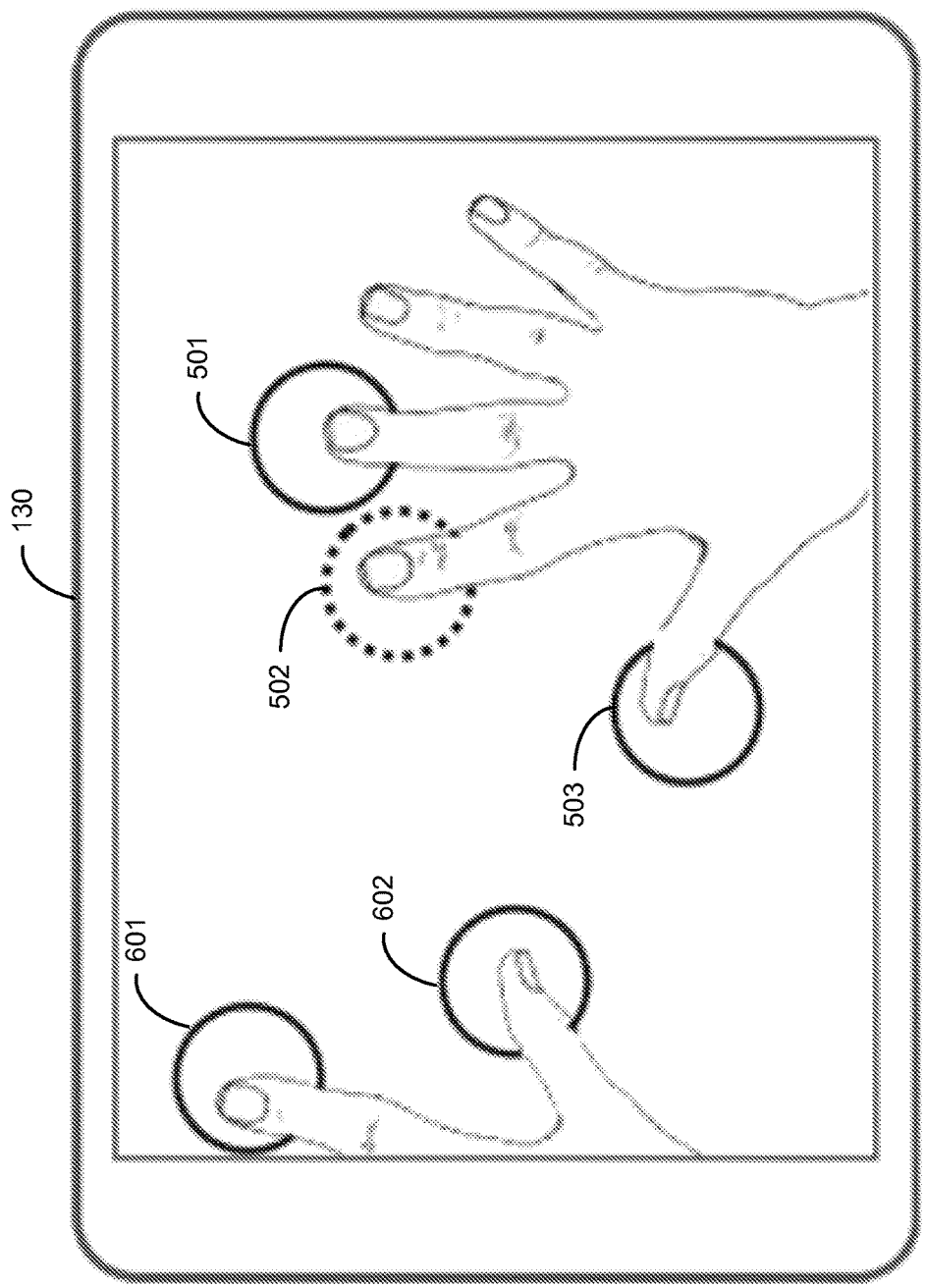
FIG. 6A illustrates an example user interface for conducting self-administered tests, according to one embodiment.
Figure 6B:
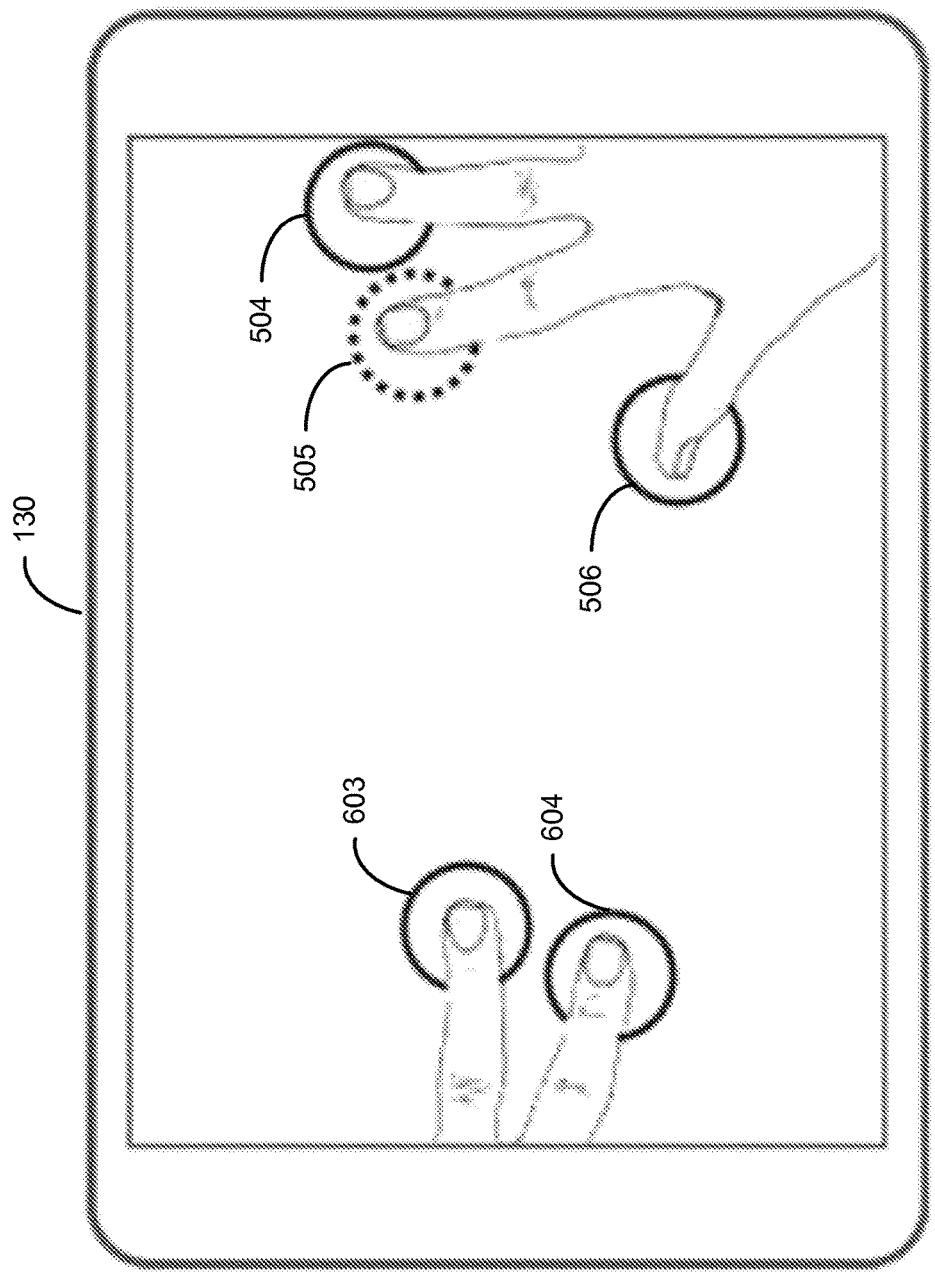
FIG. 6B illustrates an example user interface for conducting self-administered tests, according to one embodiment.

FIGS. 6A through 6C each illustrate an example user interface for conducting self-administered tests, according to one embodiment. The illustrated example user interface presented on the client device 130, such as a touchscreen, in FIG. 6A includes motion restriction regions 501, 503, 601, and 602, as well as testing region 502. The motion restriction regions 501 and 503 anchor the user's right middle finger and right thumb, respectively, thereby biomechanically isolating the right index finger. The motion restriction regions 601 and 602 anchor the user's left index finger and left thumb, respectively. Furthermore, the motion restriction regions 601 and 602 are positioned such that the user's left hand is anchored to the left edge of the client device 130 and the other fingers are prevented from touching the touchscreen of the client device 130. In addition, the centers of the motion restriction regions 501 and 503 are separated by an average distance between the tips of an adult's thumb and middle fingers. Likewise, the centers of the motion restriction regions 601 and 602 are separated by an average distance between the tips of an adult's index finger and thumb. The testing region 502 is configured to receive a touch input performed by the user's right index finger. It should be noted that the user's right hand as depicted in FIG. 6A is entirely on the touchscreen of the client device 130. As described earlier, the points of contact between the ring finger and the client device 130 and between the little finger and the client device 130 of the user's right hand are not identified by the motion measurement and monitoring module 206 as in contact with either a motion restriction region or testing region.

The illustrated example user interface presented on the client device 130 in FIG. 6B includes motion restriction regions 504 and 506 and testing region 505, as described with reference to FIG. 5B. The user interface also includes motion restriction regions 603 and 604, which anchor a user's left index and middle fingers respectively. The testing region 505 is configured for the user's right index finger to perform tasks such as tapping, making circular motions, etc., which is biomechanically isolated by the anchoring of the right thumb and middle fingers in motion restriction regions 504 and 506.

The illustrated example user interface presented on the client device 130 in FIG. 6C includes motion restriction regions 507 and 605 and testing regions 508 and 606. Motion restriction regions 507 and 605 anchor a user's right middle and left middle fingers respectively. Testing regions 508 and 606 are configured to receive touch inputs performed by a user's right index finger and left index finger respectively. In addition, the centers of the motion restriction region 507 and touch region 508, and the motion restriction region 605 and touch region 606, are separated by an average distance between the tips of an adult's index and middle fingers.

The example user interfaces illustrated in FIGS. 6A through 6C require a user to anchor fingers from both hands to the touchscreen of the client device 130 to prevent both hands from moving and also to prevent free (i.e., non-anchored) fingers from making motions that reduce the reliability of biomechanical data (as described previously). The motion restriction regions may be configured to anchor a user's fingers in a variety of arranged positions that are not necessarily symmetrical positions as illustrated. As such, non-anchored fingers are prevented from participating in compensatory actions. Further, as described previously with reference to FIG. 4, the motion measurement monitoring module 206 may dynamically monitor touch inputs. In embodiments in which the user places digits from both hands onto the touchscreen of the client device 130, the motion measurement and monitoring module 206 would maintain a record of touch inputs produced by both hands as they occur. This further ensures the reliability of biomechanical data by preventing a user from, for example, using his left index finger to produce a touch input in a testing region intended for his right index finger. Such compensatory actions may be difficult to detect in embodiments in which only one hand is instructed to make contact with motion restriction regions.

Upon reading this disclosure, those of skill in the art will appreciate still additional alternative designs for a unified communication interface providing various communication services. Thus, while particular embodiments and applications of the present disclosure have been illustrated and described, it is to be understood that the embodiments are not limited to the precise construction and components disclosed herein and that various modifications, changes and variations which will be apparent to those skilled in the art may be made in the arrangement, operation and details of the method and apparatus of the present disclosure disclosed herein without departing from the spirit and scope of the disclosure as defined in the appended claims.

What is claimed is:

1. A computer-implemented method comprising:
configuring a touch-sensitive surface of a client device configured to present a self-administered test of biomechanical motor functions of digits of a user, the touch-sensitive surface configured to include a plurality of predetermined motion restriction regions and at least one testing region, wherein:
the motion restriction regions are arranged on the touch-sensitive surface to biomechanically isolate a specified digit contacting the testing region when a plurality of other digits of the user are anchored to the motion restriction regions, and
locations of the plurality of motion restriction regions and the at least one testing region are displayed on the touch-sensitive surface;
prior to a start of the self-administered test, receiving touch inputs on the touch-sensitive surface in the motion restriction regions indicating that the plurality of other digits of the user are anchored to the plurality of motion restriction regions, and responsive to such inputs, starting the self-administered test;
receiving, during the self-administered test, first touch inputs in the testing region;

receiving, during the self-administered test, second touch inputs in at least one of the motion restriction regions, and determining from the second touch inputs whether at least one of the plurality of other digits is no longer anchored to at least one of the motion restriction regions; and responsive to determining that at least one of the plurality of other digits is no longer anchored to at least one of the motion restriction regions, indicating that touch inputs received in the testing region are invalid touch inputs.

2. The computer-implemented method of claim 1, further comprising presenting instructions to the user to anchor digits of the user to at least one of the motion restriction regions.

3. The computer-implemented method of claim 1, further comprising presenting instructions to the user to perform a first touch input using the specified digit of the user within the testing region.

4. The computer-implemented method of claim 1, wherein each received touch input comprises:
 a timestamp associated with the touch input;
 a location associated with the touch input; and
 a type of the touch input.

5. The computer-implemented method of claim 4, wherein the type of the touch input includes a designation of the touch input as one of:
 a finger-down event;
 a finger-up event; and
 a finger-move event.

6. The computer-implemented method of claim 5, wherein the determining from the touch inputs whether at least one of the plurality of other digits is no longer anchored to at least one of the motion restriction regions comprises determining that a touch input in at least one of the motion restriction regions is a finger-up event.

7. The computer-implemented method of claim 5, wherein the determining from the touch inputs whether at least one of the plurality of other digits is no longer anchored to the motion restriction region comprises determining that a touch input in at least one of the motion restriction regions is a finger-move event, and a location of the touch event is outside of at least one of the motion restriction regions.

8. The computer-implemented method of claim 1, further comprising:
 determining a number of invalid touch inputs during the self-administered test; and
 responsive to the number of invalid touch inputs exceeding a threshold, terminating the self-administered test.

9. A non-transitory computer-readable storage medium storing executable computer instructions that, when executed by a hardware processor, perform steps comprising:
 configuring a touch-sensitive surface of a client device configured to present a self-administered test of biomechanical motor functions of digits of a user, the touch-sensitive surface configured to include a plurality of predetermined motion restriction regions and at least one testing region, wherein:
  the motion restriction regions are arranged on the touch-sensitive surface to biomechanically isolate a specified digit contacting the testing region when a plurality of other digits of the user are anchored to the motion restriction regions, and
  locations of the plurality of motion restriction regions and the at least one testing region are displayed on the touch-sensitive surface;
 prior to a start of the self-administered test, receiving touch inputs on the touch-sensitive surface in the motion restriction regions indicating that the plurality of other digits of the user are anchored to the plurality of motion restriction regions, and responsive to such inputs, starting the self-administered test;
 receiving, during the self-administered test, first touch inputs in the testing region;
 receiving, during the self-administered test, second touch inputs in at least one of the motion restriction regions, and determining from the second touch inputs whether at least one of the plurality of other digits is no longer anchored to at least one of the motion restriction regions; and
 responsive to determining that at least one of the plurality of other digits is no longer anchored to at least one of the motion restriction regions, indicating that touch inputs received in the testing region are invalid touch inputs.

10. The non-transitory computer-readable storage medium of claim 9, further comprising presenting instructions to the user to anchor digits of the user to at least one of the motion restriction regions.

11. The non-transitory computer-readable storage medium of claim 9, further comprising presenting instructions to the user to perform a first touch input using the specified digit of the user within the testing region.

12. The non-transitory computer-readable storage medium of claim 9, wherein each received touch input comprises:
 a timestamp associated with the touch input;
 a location associated with the touch input; and
 a type of the touch input.

13. The non-transitory computer-readable storage medium of claim 12, wherein the type of the touch input includes a designation of the touch input as one of:
 a finger-down event;
 a finger-up event; and
 a finger-move event.

14. The non-transitory computer-readable storage medium of claim 9, wherein the determining from the touch inputs whether at least one of the plurality of other digits is no longer anchored to at least one of the motion restriction regions comprises determining that a touch input in at least one of the motion restriction regions is a finger-up event.

15. The non-transitory computer-readable storage medium of claim 9, wherein the determining from the touch inputs whether at least one of the plurality of other digits is no longer anchored to the motion restriction region comprises determining that a touch input in at least one of the motion restriction regions is a finger-move event, and a location of the touch event is outside of at least one of the motion restriction regions.

16. The non-transitory computer-readable storage medium of claim 15, further comprising:
 determining a number of invalid touch inputs during the self-administered test; and
 responsive to the number of invalid touch inputs exceeding a threshold, terminating the self-administered test.

* * * * *